United States Patent [19]

Byers et al.

[11] Patent Number: 4,571,438

[45] Date of Patent: Feb. 18, 1986

[54] PROCESS FOR PREPARING OLEFINIC ALDEHYDES AND CHEMICAL INTERMEDIATES

[75] Inventors: Jim D. Byers; Dennis S. Banasiak, both of Bartlesville, Okla.

[73] Assignee: Phillips Petroleum Company, Bartlesville, Okla.

[21] Appl. No.: 714,410

[22] Filed: Mar. 21, 1985

Related U.S. Application Data

[62] Division of Ser. No. 522,774, Aug. 12, 1983.

[51] Int. Cl.$^4$ .............................................. C07C 45/58
[52] U.S. Cl. ................................... 568/420; 568/437; 568/446; 568/459; 568/466; 568/467; 568/490; 570/182; 570/186; 570/189; 570/193; 570/216; 570/237
[58] Field of Search ............... 568/459, 467, 420, 466, 568/437, 446, 490; 570/182, 186, 189, 193, 216, 237

[56] References Cited

U.S. PATENT DOCUMENTS

| | | | |
|---|---|---|---|
| 3,971,711 | 11/1975 | Roelofs et al. | 568/459 |
| 4,212,830 | 7/1980 | Wiesner | 568/459 |
| 4,273,944 | 6/1981 | Ohno et al. | 568/459 |

OTHER PUBLICATIONS

Mori "The Total Synthesis of Natural Products", vol. 4, 1981 pp. 1, 8, 9, 10, and 11.
Synthesis, Dec. 1977, pp. 817–836, Rossi.
Tetrahedron, vol. 33, pp. 1845–1889, (1977), Henrick.

*Primary Examiner*—Werren B. Lone
*Attorney, Agent, or Firm*—S. E. Reiter

[57] ABSTRACT

A process for the preparation of olefinic aldehydes and intermediates is disclosed. The condensation of an $\alpha,\omega$-dihalide with a metal acetylide gives an acetylenic halide which can be reduced to give an olefinic halide, then oxidized to give the desired olefinic aldehyde or the acetylenic halide can be oxidized first to give an acetylenic aldehyde and then reduced to give the desired olefinic aldehyde.

12 Claims, No Drawings

PROCESS FOR PREPARING OLEFINIC ALDEHYDES AND CHEMICAL INTERMEDIATES

This application is a divisional application of copending application, Ser. No. 522,774 filed Aug. 12, 1983.

BACKGROUND OF THE INVENTION

This invention relates to a process for preparing olefinic aldehydes and chemical intermediates. In another aspect, the invention relates to certain chemical intermediates per se. In a further aspect, the invention relates to a process for the stereospecific synthesis of olefinic aldehydes. In yet another aspect, the invention relates to a process for the preparation of long-chain olefinic aldehydes.

The olefinic aldehydes prepared by the process of this invention have a variety of uses. One such use is for sex pheromones.

Sex pheromones have been employed in a variety of ways for control of insect populations. For example, traps baited with appropriate pheromone compounds or mixtures can be employed to monitor for the presence of particular insects in a field. In this way, most efficient use of pesticides or other conventional means of insect control can be applied.

Traps as just described can also be used on a larger scale such that all insect pests in a given area may be lured to a trap. This technique is most effective where low-level insect populations exist. Such a trap fulfills the dual functions of monitoring for the presence of insect infestation and removing essentially all insects from the infested area, so long as the treatment program commences when insect populations are low.

The most promising means of controlling insect populations with pheromones is by permeating the atmosphere with the particular pheromone compound or mixture to which the offending insect responds. With sufficiently high levels of pheromone in the air, the searching insect becomes confused in its search for a mating partner. Since the insect cannot distinguish the artificially released pheromone from that released by a potential sex partner, propagation is greatly reduced as the likelihood of a successful encounter with a mating partner is greatly reduced.

In order to successfully apply any of the above-described methods for insect population control, the pheromone compound or mixture appropriate to the target insect must be available in sufficient quantity and isomeric purity to allow economic use of pheromone technology on a large scale. Typically, prior art synthetic methods for the preparation of pheromones have involved numerous reaction steps, one or more of which suffer from inefficient conversion of starting material to product. Frequently, expensive protecting groups are employed which do not contribute to the overall structure of the final product, thus further increasing the cost of pheromone synthesis. Further, while some compounds are effective in relatively pure form for attraction or disruption, the presence of impurities or decomposition products can inhibit or destroy the ability of the pheromone compound to affect insect behavior. Thus, time consuming and costly separation techniques are frequently required to assure the production of an essentially pure, insect active pheromone composition.

Exemplary prior art methods are described by Roelofs, Hill, Baker and Carde in U.S. Pat. No. 3,917,711; K. Mori in "The Total Synthesis of Natural Products", Vol. 4, Chapter 1, John Wiley & Sons, 1981; R. Rossi in "Synthesis" (Dec. 1977) pp. 817–836 and C. A. Henrick in "Tetrahedron" 33, 1845(1977).

Roelofs et al disclose the preparation of Z-9-tetradecenal and Z-11-hexadecenal by the chromium trioxide/pyridine promoted oxidation of Z-9-tetradecenol and Z-11-hexadecenol, respectively. This method is unsatisfactory in that large quantities of chromium trioxide are required, low product yields are obtained and extensive product workup is required to obtain satisfactorily pure product. In addition, the alcohol precursors for the final oxidation step are obtained after six reaction steps from the starting materials, 8-chloro-1-octanol or 10-chloro-1-decanol, which in turn require a starting material such as octane-1,8-diol or decane-1,10-diol. Thus, many reaction steps, low yield and large quantities of reagents are required.

K. Mori describes the preparation of cis (Z) olefins by selective hydrogenation with such as Lindlar's catalyst. The use of such selective hydrogenation catalysts is typically accompanied by the use of a hydrogen acceptor such as quinoline. These systems are effective for selective hydrogenation of hydrocarbon substituted alkynes but are incompatible with such as halogen substituted alkynes.

Rossi also discloses the use of Lindlar's catalyst, optionally in the presence of quinoline, for the selective reduction of a variety of alkynyl compounds. The starting materials employed in all examples shown are ethers, esters, alcohols or acids. Such starting materials would all require one or more additional process steps to achieve the aldehyde products desired for pheromone applications, such as the oxidation disclosed by Roelofs.

Henrick details additional exotic routes devised for the stereospecific preparation of cis-olefinic compounds useful as pheromones such as Wittig Chemistry, ylide chemistry and the like. In addition, Henrick describes a variety of oxidation processes which have been employed in efforts to overcome the disadvantages of the chromium trioxide-pyridine promoted oxidation discussed above. Each method described produces sufficient levels of impurities to create a purification problem when carried out on a large scale.

It is therefore an object of this invention to provide a process for the preparation of olefinic aldehydes. It is a further object of this invention to provide in high stereoisomeric purity cis-olefinic aldehydes. It is another object of this invention to provide a simple, economical process for the preparation in high stereoisomeric purity of cis-olefinic aldehydes useful as pheromones. It is yet another object of this invention to provide a process for the preparation of acetylenic halides, acetylenic aldehydes and olefinic halides. It is another object of this invention to provide acetylenic halides, acetylenic aldehydes and olefinic halides useful as chemical intermediates.

SUMMARY OF THE INVENTION

In accordance with one aspect of the present invention, an olefinic aldehyde is prepared by:
(a) Reaction of an $\alpha,\omega$-dihalide with a metal acetylide to give an acetylenic halide;
(b) Selective hydrogenation of the acetylenic halide obtained in step (a) to give an olefinic halide;
(c) Oxidation of the olefinic halide product from step (b) to give an olefinic aldehyde.

In accordance with another aspect of the present invention, an olefinic aldehyde is prepared by:

(a) Reaction of an α,ω-dihalide with a metal acetylide to give an acetylenic halide;
(c') Oxidation of the acetylenic halide product from step (a) to give an acetylenic aldehyde;
(b') Selective hydrogenation of the acetylenic aldehyde obtained in step (c') to give an olefinic aldehyde.

In accordance with a further aspect of the present invention, the α,ω-dihalide starting material for step (a) is prepared by halogenation of an α,ω-diol or α,ω-diene.

In accordance with another aspect of the invention, an acetylenic halide is prepared by reaction of an α,ω-dihalide with a metal acetylide.

In accordance with yet another aspect of the invention, an olefinic halide is prepared by the selective hydrogenation of an acetylenic halide.

In accordance with another aspect of the invention, an acetylenic aldehyde is prepared by oxidation of an acetylenic halide.

In accordance with yet another aspect of the invention, novel acetylenic halides, olefinic halides and acetylenic aldehydes are provided.

DETAILED DESCRIPTION OF THE INVENTION

A variety of suitable α,ω-dihalide compounds are commercially available which are operable according to the inventive synthetic scheme set forth above. However, one need not be limited to those compounds which are commercially available. Although any suitable α,ω-dihalide can be employed, in general, one can prepare α,ω-dihalides of the formula $$X-CH_2-(CR_2)_y-CH_2-X \quad (I)$$

where y is broadly 1 to 20, preferably 1 to 10, X is Cl, Br or I and each R is independently H, $C_1$-$C_{20}$ alkyl, cycloalkyl, aryl, aralkyl or alkaryl from suitable starting materials such as, for example, α,ω-diols and α,ω-dienes by methods well known in the art such as, for example, addition of gaseous or aqueous hydrogen halide to an α,ω-diol or addition of gaseous hydrogen halide to an α,ω-diene in the presence of a peroxide.

Step (a):

The starting materials for step (a) are (1) an α,ω-dihalide and (2) a metal acetylide. Preferably employed are an α,ω-dihalide of the formula (1) and a metal acetylide prepared from an alkyne of the general formula $$H-C\equiv C-CH_2-(CR_2)_x-H \quad (II)$$

where x is broadly 0-20, preferably 0-10, and R is as defined above. Although any suitable metallating agent can be employed, the most preferred metallating agent is n-butyl lithium due to its ready availability and ease in handling. Also, other preferred compounds include those, for example, of the structure R'M, where:
R' = $C_1$-$C_4$ hydrocarbyl or $NH_2$
M = Li, Na.

The resulting metal acetylide has the general formula $$M-C\equiv C-CH_2-(CR_2)_x-H$$

where x, R and M are as defined previously.

Promoters are desirable to increase the rate of the desired condensation reaction. Some examples of operable donor compounds include ethylene diamine, tetramethylenediamine, tetramethylurea, pyridine, dioxane and the like. Preferred donor compounds are diglyme (diethylene glycol dimethyl ether), triglyme (triethylene glycol dimethyl ether), tetraglyme (tetraethylene glycol dimethyl ether), hexamethylphosphorus triamide, 1,3-dimethyl-3,4,5,6-tetrahydro-2(1H)-pyrimidinone and 1,3-dimethyl-2-imidazolidinone and mixtures thereof.

Solvents such as tetrahydrofuran (THF) can optionally be employed. When used, solvents are preferably dried such as, for example, by percolation through a bed of Alcoa H151 Alumina.

Although any ratio of dihalide (I) to alkyne (II) is operable, the ratio of dihalide (1) to alkyne (II) employed is generally maintained above one to minimize the formation of dialkynyl product. Preferably, dihalide to acetylide ratios of 1:1 to about 4:1 are employed. Most preferably, ratios of about 1.1:1 to about 2:1 are used.

Although any suitable amount of metallating agent can be employed, for best results, the metallating agent, such as R'M, is generally employed in about equimolar amounts relative to the alkyne charged. Typically, the metallating agent is added slowly to a chilled (below about 10° C.) solution of the alkyne in a solvent such as THF, diglyme or the like.

The promoter, when employed, is charged in any amount, although it is preferably employed in the amount of about 0.5-1 mole per mole of metallating agent when added solvent is also present. When the promoter is also used as solvent, e.g. diglyme, it is preferably charged in the amount of about 2-4 moles per mole of metallating agent.

The reaction of the α,ω-dihalide and the metal acetylide can be carried out at any suitable temperature and for any appropriate time as can be readily determined by one skilled in the art. Typical reaction conditions employed include a preferred temperature range of about 90°-150° C., with 100°-110° C. most preferred. Suitable reaction time is about 2-8 hours, with 3-5 hours preferred. Reaction generally is carried out at atmospheric pressure, although most any pressure can be employed. It is desirable, although not essential, that reaction be carried out under an inert atmosphere, employing an inert gas such as $N_2$, Ar or the like.

Any suitable method for product isolation can be employed. A typical reaction workup involves first adding water, then separating the organic phase and distilling. Alternatively, a nominal amount of water can be added to hydrolyze active metal species, thereby eliminating the need for a phase separation. Thus, once the required minimal amount of water is added, the reaction mixture can be distilled directly. The distillation at this stage must be fairly efficient since the following fractions are typically recovered:

(1) Water
(2) Solvent
(3) Unreacted dihalide (I) which can be recycled back for reaction with additional metal acetylide;
(4) Product alkynyl halide, having the following formula $$H-(CR_2)_x-CH_2-C\equiv C-CH_2-(CR_2)_y-CH_2-X \quad (III)$$

where x, y, X and R are as defined above;
(5) Pot residue contains dialkynyl adduct and other unidentified heavy materials.

Step (b):

As indicated above, the sequence in which steps (b) and (c) (selective hydrogenation and oxidation, respectively) are carried out is not critical. Thus, the selective hydrogenation reaction can be carried out employing the alkynyl halide product (III) or the alkynyl aldehyde of the following formula:

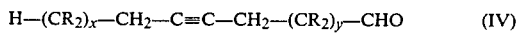

$$H-(CR_2)_x-CH_2-C\equiv C-CH_2-(CR_2)_y-CHO \quad (IV)$$

where x, y and R are as defined above, which would be obtained by first carrying out step (c') followed by step (b').

Suitable catalysts for the selective hydrogenation step are well known in the art. Preferred are those which are capable of promoting alkyne hydrogenation to give alkene (V) or (VI) with a selectivity of at least 90%

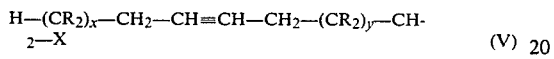

$$H-(CR_2)_x-CH_2-CH\equiv CH-CH_2-(CR_2)_y-CH_2-X \quad (V)$$

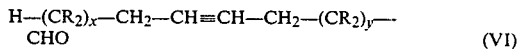

$$H-(CR_2)_x-CH_2-CH\equiv CH-CH_2-(CR_2)_y-CHO \quad (VI)$$

where x, y, X and R are as defined above.

Selective hydrogenation refers both to the amount of hydrogen consumed in the hydrogenation step, i.e., one mole per mole of alkyne to give an alkene or two moles per mole of alkyne to give an alkane, as well as to the orientation of hydrogen addition where an alkene product is obtained. For example, where cis-alkene product is desired, selectivity to cis-alkene (compared to trans-alkene) of at least 90 mol %, preferably at least 95 mol %, most preferably at least 97 mol % is desired. Catalysts such as Lindlar's catalyst (5 wt % Pd on CaCO₃ modified with Pb (OAc)₂) and Ni(OAc)₂ reduced with NaBH₄ optionally supported on a support such as silica meet these specifications. Where trans-alkene product is desired, high selectivities to same can be achieved, for example, by reduction of a protected acetylenic aldehyde with Na in liquid ammonia or reduction with hindered organoaluminum hydrides, followed by regeneration of the aldehyde.

Lindlar's catalyst is typically employed suspended in saturated hydrocarbon solvents, preferably those with about 5-12 carbon atoms.

Reaction parameters include a preferred reaction pressure of atmospheric to about 200 psig, although most any pressure can be employed. Suitable reaction temperatures include about −60° C. to about room temperature (25° C.) with temperature preferably maintained below about 0° C. Most preferably, a reaction temperature of −20° to about 0° C. will be employed. Reaction time can broadly be 30 minutes to about 8 hours, with 60 minutes to about 120 minutes preferred.

Solvent and substrate, either alkynyl halide (III) or alkynyl aldehyde (IV) can be employed in any suitable ratio as readily determined by one skilled in the art. Suitable ratios are about 10:1 to about 1:10 parts solvent to substrate. Preferably, for ease of handling and product recovery, solvent and substrate are charged to the reactor in roughly equal volumes.

The total weight of catalyst to be used can be readily determined by one skilled in the art. Preferably, the amount of catalyst employed is 1-5 wt % of the substrate charged. Most preferably 2-3 wt % of catalyst is used, for most efficient use of catalyst and high product selectivities.

Hydrogen is generally fed on demand, i.e., as it is taken up by the reaction mixture. Thus, for example, where reaction is carried out at 120 psig, reactor pressure may be allowed to drop to about 60 psig, then the pressure will be returned to about 120 psig by introducing more hydrogen. Alternatively, reaction may be run at atmospheric pressure with continuous hydrogen uptake from a manometer assembly as hydrogen is consumed by reaction.

Reaction workup consists of catalyst removal, for example by filtration, and solvent removal by such techniques as flash distillation. The resulting crude product of the following formula

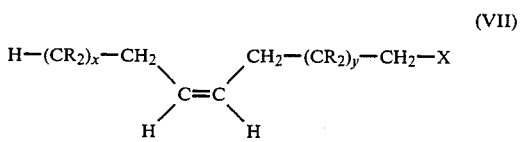

(VII)

is then ready for the next conversion step. Alternatively, where alkynyl aldehyde (IV) was employed as the starting material for the selective hydrogenation step, crude reaction product (after catalyst removal) is ready for purification by such as distillation for recovery as final product having the following structure:

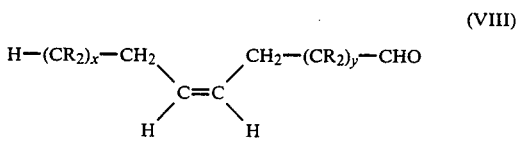

(VIII)

Recovered catalyst removed by such as filtration can be recycled for additional hydrogenation reactions.

Step (c):

The oxidation step broadly involves conversion of the —CH₂—X moiety of the starting material, alkenyl halide (V) or alkynyl halide (III), to an aldehyde, i.e., —CHO, moiety. Several techniques for accomplishing the desired conversion are well known in the art. For example, hydrolysis of the halide to an alcohol, followed by oxidation will give the desired aldehyde product. A preferred method for accomplishing the desired conversion is a one-step oxidation of the —CH₂—X moiety.

The preferred reagents employed in step (c) include the crude alkenyl halide (V) from step (b) or the crude alkynyl halide (III) from step (a), sodium bicarbonate, an amine oxide, and, optionally, a solvent. These reagents allow the desired conversion to be carried out in one step with minimal double bond isomerization and good yields of the desired products.

Amine oxides in general are suitable. Preferred compounds include pyridine N-oxide, trimethylamine N-oxide, and triethylamine N-oxide.

Suitable solvents include the glymes, such as glyme, diglyme, triglyme, and tetraglyme; aromatics, such as toluene and xylenes; C₈-C₁₄ saturated hydrocarbons such as decane; ethers such as THF; polar aprotic solvents such as dimethylformamide (DMF), dimethylsulfoxide (DMSO) and sulfolane.

Any suitable amount of amine oxide as can be readily determined by one skilled in the art can be employed. Typically, a 1:1 to about 4:1 mole ratio of amine oxide to substrate is employed, with ratios of about 1.2:1 to about 2:1 preferred. NaHCO₃ can be employed in any suitable amount. Preferably, NaHCO₃ will be employed in the range of about 1:1 to about 4:1 NaHCO₃ to substrate. It is especially preferred that NaHCO₃ be employed in an amount at least twice the molar amount of substrate employed. This is because the NaHCO₃ disproportionates under typical reaction conditions to give $Na_2CO_3$ and $H_2O$ and $CO_2$. Thus, up to one-half of the reactant, NaHCO₃, charged to the reaction may become unavailable for the desired oxidation reaction.

When the alkenyl halide (V) or alkynyl halide (III) starting material is a chloride (X=Cl), sodium iodide, NaI, may additionally be added to the reaction mixture. Addition of NaI in any suitable amount, preferably from about 1 to about 10 mol % based on substrate serves to enhance the rate of the oxidation reaction.

When solvent is employed, any suitable ratio of solvent and substrate, alkenyl halide (V) or alkynyl halide (III), can be used. Generally, a 3:1 to about 1:3 solvent to substrate mix is employed.

Reaction is preferably, although not necessarily, carried out at atmospheric pressure under an inert atmosphere ($N_2$, Ar or the like). Any suitable temperature and pressure may be employed. Temperatures employed are preferably about 90°–150° C., with 105° to about 130° C. most preferred. Any reaction time is suitable, although generally reaction times of 30 minutes to about 8 hours are employed, with about 1–3 hours preferred.

Any suitable methods for product isolation can be employed. A typical reaction workup involves several steps. First, reaction mixture is cooled to about 25° C. to precipitate solid materials. An equal volume of a suitable organic solvent such as ethyl acetate or diethyl ether is added, and the mixture filtered. The solid-free liquid is washed once with an equal volume of water. Crude product alkynyl aldehyde (IV) or alkenyl aldehyde (VI) is then ready for solvent removal by, for example, distillation. Clean product is then recovered, typically by distillation at reduced pressure. For example, Z-11-hexadecenal (VIII); R=H; x=3; y=8; is recovered at about 125° C. and a distillation pressure of 0.3–0.4 mm Hg.

The process of this invention is useful for the stereospecific synthesis of sex pheromones such as Z-11-hexadecenal (*Chilo suppressalis, Heliothis virescens* and *Heliothis zea*), Z-9-hexadecenal (*Heliothis armiger, Heliothis virescens,* and *Heliothis zea*), Z-11-tetradecenal (*Argyrotaenia citrana, Choristoneura fumiferana, Croesia askoldana, Heliothis armiger* and *Hoshinoa adumbratara*), Z-9-tetradecenal (*Euxoa acornis, Fishia derelicta, Heliothis armiger, Heliothis punctiger, Heliothis virescens,* and *Polia tacoma*), and the like.

EXAMPLES

Examples I–VI demonstrate exemplary preparations of α,ω-dihalides suitable for use in the invention. Examples VII–XV demonstrate step (a), Example XVI demonstrates step (b), Example XVII demonstrates step (c), while Example XVIII demonstrates the interchangeability of steps (b) and (c).

EXAMPLE I

A 5 liter jacketed 3-necked round bottom flask was equipped with a mechanical stirrer, a reflux condenser, and an addition funnel. A quantity of 768 grams (1086 milliliters, 8.4 mole) of concentrated aqueous HBr (48 wt. %) was placed in the reactor, followed by 696 g (4 mol) of 1,10-decanediol. 940 grams (532 milliliters, 8.4 mole) of concentrated $H_2SO_4$ (96 wt. %) was then added dropwise over several minutes. Steam was then introduced through the vessel jacket, raising the temperature of the reaction contents to about 100°–105° C. Steam was applied for about five hours, the reactor allowed to cool for about thirty minutes, then 2 L of water added, stirred briefly and allowed to stand overnight. The aqueous layer was decanted and the reactor contents then washed with about 2 L of saturated sodium bicarbonate solution. If necessary to assure neutral or slightly basic pH, $Na_2CO_3$ was added. Optionally, about 300–500 mL of chlorobenzene could be added to aid emulsion breaking. The aqueous layer was discarded and the organic layer distilled to recover dibromide product boiling at 159°–163° C. @ 5–6 mm Hg. A 54 mol % yield (640 g) of 1,10-dibromodecane (>95 wt. % purity) was obtained.

EXAMPLE II

A 5 liter, 3-necked flask was equipped with a mechanical stirrer, a fritted bubbler and a gas outlet adapter. A solution of 1,9-decadiene (500 g, 3.6 mol) and 5 g of benzoyl peroxide in 1 L of n-hexane was placed in the flask, which was chilled to about 5° C. and maintained at 5°–10° C. while HBr gas was bubbled through. HBr gas was introduced over a 7 hour period, at which time the reaction mixture was poured into about 2 L of water, then neutralized by addition of NaHCO₃. About 200 mL of diethyl ether was added, the solution thoroughly mixed, then allowed to stand overnight. After settling, the aqueous layer was separated and extracted with about 200 mL of ether. The organic layers were then combined, dried over MgSO₄, filtered, and stripped of solvent on a rotary evaporator. Distillation of the crude product through a two foot packed glass column gave about 625 g (58 mol % yield) of 1,10-dibromodecane.

EXAMPLE III

A 3 liter, 3-necked round bottom flask was equipped with a mechanical stirrer, a fritted bubbler and a gas outlet adapter. The flask was charged with 1000 g (5.7 mol) of 1,10-decanediol flakes. The vessel was then heated to about 125° C. to melt the diol, and anhydrous HBr was bubbled into the molten diol. About 2.5 pounds (1135 g, 14.0 mol—2.4 mol excess) of HBr were added over a 2 hour period. When HBr addition was complete, about 10 mL of concentrated $H_2SO_4$ were added. The reaction mixture was stirred for an additional 4 hours at about 125°–145° C. before cooling to room temperature. About 1.5 L of saturated NaHCO₃ was added to the dark reaction mixture, which was stirred for about 30 minutes. pH paper indicated that the solution was neutral. The organic layer was separated and distilled, giving 1550 g (90 mol % yield) of 1,10-dibromodecane.

EXAMPLE IV

A 12 liter, 3-necked round bottom flask equipped as described in Example III was charged with 4000 g (23.0 mol) of 1,10-decanediol. The pot was warmed to melt the diol, then anhydrous HBr bubbled slowly through the molten diol, so that after about 7½ hours, about 4400 g of HBr (54.4 mol—2.4 molar excess) had been introduced. Reaction temperature was maintained at about 135° C. during the HBr addition. Once HBr addition was terminated, the reaction mixture was allowed to cool to about 100° C., when 2.5 L of saturated NaH- CO₃ was added slowly. To aid neutralization, an additional 200 g of solid NaHCO$_3$ was added also. The aqueous layer still tested acidic by pH paper, so the aqueous layer was removed and the organic layer washed with another 2.5 L of saturated NaHCO$_3$. The solution was stirred for about 10 minutes, then allowed to stand overnight. The layers were then separated and the organic layer distilled under vacuum to give 1,10-dibromodecane in good yield (greater than 90%).

EXAMPLE V

A 1 liter, 3-necked round bottom flask equipped as described above was charged with 300 g (2.1 mol) of 1,8-octanediol. The vessel was heated to melt the diol. When the reactor contents reached 100° C., rapid introduction of anhydrous HBr commenced. Reactor temperature was allowed to rise to about 135° C. and maintained at that level for about 5 hours while HBr addition continued. HBr addition was stopped, the solution allowed to cool to room temperature, then about 1 L of water added. There was no reaction noted upon addition of a few grams of NaHCO$_3$. About 700 mL of diethyl ether was added, the solution stirred and allowed to settle, then the water layer separated and discarded. The organic layer was dried over MgSO$_4$, filtered, and solvent removed on the rotary evaporator. Pure product was obtained by vacuum distillation at 0.2 mm Hg. An 82 mol % yield (460 g) of pure 1,8-dibromooctane was obtained.

EXAMPLE VI

A 2 liter, 3-necked round bottom flask was equipped with an addition funnel, an argon inlet valve, a condenser and a mechanical stirrer. The vessel was charged with 174.3 g (1 mol) of 1,10-decanediol slurried in about 500 mL of dry diethyl ether, then purged with oxygen-free argon. A solution of 85 mL of PBr$_3$ in 250 mL of diethyl ether was charged to the addition funnel, then added dropwise to the diol suspension at a rate so as to maintain gentle reflux. PBr$_3$ addition was complete in about 3 hours, then reflux maintained for an additional 16 hours. The reaction mixture was then poured over about 700 mL of ice water. The layers were separated, and the aqueous layer extracted two times with 250 mL aliquots of with diethyl ether. The combined organic layers were washed two times with 500 mL aliquots of saturated NaHCO$_3$ and once with about 500 mL of water. The organic layer was then dried over MgSO$_4$, filtered, and solvent removed on the rotary evaporator. About 220 g (73.3 mol % yield) of pure dibromide was obtained by distillation (125° C. @ 2 mm Hg).

EXAMPLE VII

A 2 liter round bottom flask equipped with a magnetic stir bar was charged with 82.5 g (1 mol) of 1-hexyne in about 500 mL of THF, chilled to about −10° C. n-Butyllithium in hexane (645 mL, 1.55M =1 mol) was added dropwise as rapidly as possible while maintaining the pot temperature at about −10° C. under an argon atmosphere. Once butyllithium addition was complete, the reaction mixture was stirred for an additional 2 hours, maintained at a temperature up to about 0° C.

This example describes a typical preparation of hexynyllithium employed in the following alkynylation reactions.

EXAMPLE VIII

A 3 liter, 2-necked round bottom flask was equipped with a magnetic stir bar, an inlet valve and a septum. After being purged with an argon atmosphere, the flask was charged with 615 g (2.1 mol) of 1,10-dibromodecane in 350 mL of THF and 125 mL of hexamethylphosphorus triamide. A solution containing about 1 mol of hexynyllithium, prepared as described above, was then added to the solution of dibromide via the septum. The reaction mixture was allowed to stir overnight, then quenched by pouring over about 1 L of water. The reaction mixture was diluted with about 500 mL of hexane, phases separated and the organic layer washed twice with 500 mL aliquots of water. The organic layer was then dried over MgSO$_4$, filtered, solvent stripped on the rotary evaporator, then vacuum distilled through a 2 foot column packed with ¼" glass helices. About 104 g (35 mol % yield) of hexadecynyl bromide was obtained with a boiling point of 135° C. @ 0.3 mm Hg.

EXAMPLE IX

A 3 liter 3-necked round bottom flask equipped with a mechanical stirrer, addition funnel and reflux condenser was charged with 2 moles of hexynyllithium prepared as described above (Example VII), in about 200 mL of hexane under an argon atmosphere at about −10° C. To this was added 4 moles (1200 g) of 1,10-dibromodecane in one batch. Once thorough mixing was achieved, 250 mL of hexamethylphosphorus triamide was rapidly added. The reaction mixture was then allowed to stir overnight at room temperature under an argon atmosphere.

Workup was accomplished by pouring the reaction mixture over about 1 L of water, diluting with about 500 mL of hexane, shaking together and then separating layers. The aqueous layer was extracted with about 500 mL of ether, then the combined organic layers dried over MgSO$_4$, filtered and solvent removed on the rotary evaporator. Product was recovered by vacuum distillation as described above to yield 410 g of hexadecynyl bromide and an additional 70 g of hexadecynyl bromide mixed with unreacted dibromide, for a yield of >70 mol % based on starting hexynyllithium.

EXAMPLE X

An oven-dried, 3-necked, 500 mL round bottom flask equipped with a reflux condenser and a magnetic stirrer was charged with 100 mL of THF, 11 g of 1-hexyne (0.125 mol) and tetradecane (glc internal standard). The solution was cooled to below 10° C. and dropwise addition of n-butyllithium begun. A total of 94 mL of 1.6M solution of n-BuLi in hexane (0.15 mol) was added, with temperature maintained below 10° C. When n-BuLi addition was complete, solution was stirred for an additional 30 minutes, then 75 g of 1,10-dibromodecane (0.25 mol) was added in one slug. About 15 minutes after dibromide addition, dropwise addition of hexamethylphosphorus triamide (HMPTA, 26 mL, 0.125 mol) was commenced. Addition rate was controlled so as to maintain a reaction temperature below 30° C. Once HMPTA addition was complete, the reaction mixture was warmed to reflux (60°-70° C.) for 3-4 hours. Glc analysis of the final reaction mixture indicated an alkynyl bromide yield of about 53 mol %.

EXAMPLE XI

Several alkynylation reactions were carried out employing diglyme as the promoter. All runs were carried out in an oven-dried, 3-necked, 500 mL round bottom flask equipped with a reflux condenser and a magnetic stirrer. Variable amounts of diglyme, as indicated in Table I, were employed, along with 11 g of 1-hexyne (0.125 mol) and tetradecane as glc internal standard. The solution of diglyme, 1-hexyne and tetradecane was chilled to below 10° C. and 95 mL of 1.6M n-butyllithium (n-BuLi; 0.15 mol) was added dropwise. Temperature was maintained below 10° C. during n-BuLi addition. About 30 minutes after n-BuLi addition was completed, 75 g of 1,10-dibromodecane (0.25 mol) was added in one slug. The reaction mixtures were then heated to about 80°–120° C. for 3–5 hours.

TABLE I

| Run | Diglyme | Reaction Conditions Temp., °C. | Time, Hr. | Yield of alkynyl bromide* |
|---|---|---|---|---|
| 1 | 100 mL | 82 | 3 | 41 |
| 2 | 100 | 93 | 3 | 62 |
| 3 | 100 | 114 | 3.5 | 71 |
| 4 | 80 | 110 | 4.5 | 43 |
| 5 | 80 | 99 | 4.5 | 38 |
| 6 | 80 | 99 | 4.5 | 53 |

*Determined by glc; as mol % based on moles of 1-hexyne charged.

The results of these experiments demonstrate that diglyme is a suitable promoter for the alkynylation of alkyl bromides with alkynyl lithium compounds.

EXAMPLE XII

A 3-necked, 12 L round bottom flask equipped with a mechanical stirrer, a Dean-Stark trap, a condenser and an addition funnel was charged with 395 g (4.8 mol) of 1-hexyne and 2.25 L of dry diglyme under a nitrogen atmosphere. The reaction vessel was chilled to about 0° C. with an ice-salt bath, then dropwise addition of n-butyllithium (3 L, 1.6M in hexane; 4.8 mol) was commenced. Reaction temperature was maintained below 10° C. during n-BuLi addition. Reactor contents were stirred for an additional 30 minutes after n-BuLi addition was complete, then 2880 g of 1,10-dibromodecane (9.6 mol) were added in one slug. The ice-salt batch was replaced with a heating mantle, and the reaction mixture heated to about 95°–100° C. for about 3 hours. Hexane was removed via the Dean-Stark trap and returned to the reaction vessel as needed to aid control of the reaction temperature.

After cooling the reaction mixture to room temperature, reaction was quenched by addition of about 2 L of water. The organic phase was separated and distilled directly @ 5 mm Hg using a silvered one foot glass column packed with glass rings. A 55 mol % distilled yield of the desired alkynyl bromide with a boiling point of about 183° C. was obtained.

It was noted during the distillation that the pot temperature should be maintained below about 230° C. to minimize decomposition of product by dehydrohalogenation.

EXAMPLE XIII

Several alkynylation reaction were carried out employing tetraglyme as the promoter. All runs were carried out employing the procedure set forth in Example XI. Thus, 100 mL of tetraglyme, 11 g of 1-hexyne, 95 mL of 1.6M (in hexane) n-BuLi, 75 g 1,10-dibromodecane and tetradecane internal standard were employed. Reaction mixtures were heated to 100°–120° C. for about 2 hours. The average glc yield for 8 such runs was 52 mol %, with a high of 61 mol % and a low of 35 mol %.

Example XIV

A number of reactions were carried out employing a variety of promoters or combinations of promoters following the general procedure set forth in Example XI. Solvents were employed to dissolve the reaction components, while the promoters employed were added about 30 minutes after the addition of dibromide was complete.

TABLE II

| Run | Solvent, mL | Promoters, mL* 1 | 2 | Reaction Conditions Temp., °C. | Time, hr. | Yield of alkynyl bromide, mol % |
|---|---|---|---|---|---|---|
| 1 | THF, 200 | TMEDA, 14 | — | 70 | 1 | 29 |
| 2 | THF, 100 | TMEDA, 14 | — | 70 | 4 | 33 |
| 3 | THF, 100 | TMEDA, 42 | — | 70 | 3 | 20 |
| 4 | THF, 100 | TMEDA, 14 | HMPTA, 2.2 | 73 | 3.5 | 27 |
| 5 | Diglyme, 100 | TMEDA, 14 | — | 90 | 3 | 37 |
| 6 | Diglyme, 100 | TMEDA, 7 | — | 90 | 3 | 36 |
| 7 | Dioxane, 100 | — | — | 100 | 2.5 | 31 |
| 8 | Diglyme, 100 | Pyridine, 36 | — | 100 | 3.5 | 17 |
| 9 | THF, 100 | Pyridine, 36 | — | 72 | 3 | 39 |
| 10 | THF, 100 | TMEDA, 14 | Pyridine, 12 | 70 | 3 | 35 |
| 11 | THF, 100 | TMU, 55 | — | 73 | 3 | 13 |
| 12 | THF, 150 | EDA, 10 | — | 25 | 18 | 21 |
| 13 | THF, 100 | DMF, 100 | EDA, 10 | 63 | 2 | trace |
| 14 | THF, 50 | TEPA, 80 | — | 73 | 1.5 | 9 |
| 15 | THF, 200 | TEPA, 20 | — | 73 | 1 | 29 |
| 16 | Diglyme, 120 | TEPA, 48 | — | 65 | 1 | 22 |

*Legend:
TMEDA = tetramethylene diamine
HMPTA = hexamethylphosphorus triamide
TMU = tetramethylurea
EDA = ethylene diamine
DMF = dimethylformamide
TEPA = tetraethylene pentamine The results of these experiments indicate that a variety of donor compounds are operable as donors in the alkynylation reaction of this invention.

EXAMPLE XV

A 3-necked, 3 L round bottom flask equipped with a mechanical stirrer and an addition funnel was charged with 82 g of 1-hexyne (1 mol) in 250 mL of dry THF under an inert atmosphere, then chilled to −10° C. n-Butyllithium, 10.5M in hexane (105 mL, 1.1 mol) was added dropwise so that a reaction temperature of −10° C. was maintained. Following complete addition of the n-BuLi, the reaction mixture was stirred for two additional hours maintained at −10° to 0° C., then 460 g of 1,8-dibromooctane (1.7 mol) was added in one slug. The mixture was stirred for about 15 minutes after dibromide addition was complete, when about 150 mL of hexamethylphosphorus triamide was added rapidly. Reaction temperature was maintained below about 10° C. during HMPTA addition. Cooling was then removed from the reaction vessel, and the contents stirred at room temperature for about 18 hours.

adjusted to the desired level and reaction allowed to proceed. Hydrogen was intermittently added to maintain the desired reaction pressure. Reaction time, temperature and hydrogen pressure are indicated in Table III.

Where catalyst recycle is indicated (designated by an * in the table), catalyst was allowed to settle by discontinuing stirring, then liquid was removed via a dip tube and fresh alkynyl bromide was added to the autoclave in additional hexane solvent.

Reaction was quenched by passing nitrogen over the catalyst, which was then removed by filtration through a bed of Celite filter aid. Solvent was removed on the rotary evaporator and the resulting product ready for step (c).

TABLE III

|     | Reagents      |                      | Reaction Conditions |           |           |
| --- | ------------- | -------------------- | ------------------- | --------- | --------- |
| Run | Dibromide, g  | Catalyst Supplier, g** | $H_2$ Press, psig | Time, min | Temp., °C. |
| 1   | 100           | Alfa, 4              | 120                 | 35        | −12−0     |
| 2*  | 100           | —                    | 120                 | 70        | −8−0      |
| 3   | 95            | Strem, 2.5           | 120                 | 90        | −11−0     |
| 4   | 200           | Strem, 4             | 120                 | 40        | −5−0      |
| 5   | 200           | Sterm, 5             | 120                 | 110       | −6−0      |
| 6   | 203           | Alfa, 3.5            | 46                  | 720       | 2−4       |
| 7   | 205           | Alfa, 6              | 50                  | 45        | 8−15      |
| 8*  | 205           | —                    | 50                  | 60        | ND        |
| 9   | 55            | Alfa, 4              | 49                  | 24        | 6−7       |
| 10  | 100           | Alfa, 5              | 120                 | 46        | −11−0     |
| 11  | 100           | Alfa, 2              | 120                 | 120       | −9−0      |
| 12  | 200           | Alfa, 5              | 120                 | 50        | −4−2      |

*Recycle of same catalyst with additional alkynyl bromide.
**Alfa catalyst is provided by Alfa Products, Thiokol/Ventron Division P.O. Box 299, 152 Andover Street Danvers, Massachusetts 01923
Strem catalyst is provided by Strem Chemicals, Inc. P.O. Box 108 Newburyport, Massachusetts 01950

Reaction was quenched by adding about 500 mL of water, then the organic layer separated and subjected to vacuum distillation. A 64 mol % yield (175 g) of alkynyl bromide was recovered with a boiling point of about 115° C. @ 0.25 mm Hg.

Example XVI

A number of hydrogenation reactions were carried out employing pure alkynyl bromide prepared as described in Examples VII–XV according to the following typical procedure. Pure, distilled alkynyl bromide, about 200 mL of hexane solvent and 5 wt. % Pd on $CaCO_3$ modified with lead acetate (supplied by Alfa or Strem) were loaded into a 1 L stainless steel Autoclave Engineers Magnedrive stirred tank reactor. After the head of the reactor was bolted in place, nitrogen was flushed through the autoclave for about 5 minutes. The exit valve was then closed, and a nitrogen pressure of 100 psig supplied. The pressure was vented, then increased to 100 psig and vented twice more. Finally, a nitrogen pressure of 100 psig was provided and the stirrer was turned on for 1-2 minutes, then the stirrer stopped and nitrogen pressure vented. This procedure was repeated four times. Then four pressure/vent cycles with hydrogen (120 psig; no stirring) were carried out then three pressure/vent cycles with hydrogen with the stirrer running. Finally, the hydrogen pressure was In all cases, the yield of alkenyl bromide was essentially quantitative. $^{13}C$ NMR analysis of representative samples verified the absence of alkyne unsaturation and that the stereochemistry of the double bond was cis.

EXAMPLE XVII

Numerous reactions were carried out employing the alkenyl bromide products prepared as described in Example XVI according to the following typical procedure. A 3-necked round bottom flask equipped with a mechanical stirrer, nitrogen inlet, Dean-Stark trap, condenser and sample introduction port was loaded with alkenyl bromide, sodium bicarbonate, pyridine N-oxide and, optionally, solvent. The reaction mixture was heated to about 125°-130° C. and maintained at that temperature for about 90 minutes. Once the reaction mixture cooled below about 50° C., solvent such as pentane or ethyl acetate was added, the reaction mixture passed through a sintered glass filter coated with Celite, then distilled. Alternatively, the diluted reaction mixture can be poured over an equal volume of water, about 2 volume % isopropanol added as needed to aid emulsion breaking, then the organic layer separated and solvent removed on the rotary evaporator before product is subjected to vacuum distillation. The amounts of reagents as well as the yield of product are reported in Table IV.

TABLE IV

|     | Reagents |      |      |      | Yield of |
| --- | -------- | ---- | ---- | ---- | -------- |
| Run | Alkenyl bromide, g | $NaHCO_3$, g | Pyridine-N—oxide, g | Solvent mL | cis-11-hexadecenal, mol % |
| 1[d] | 100 | 55 | 63 | diglyme, 100 | 55 |
| 2[c] | 100 | 55 | 63 | none | 45 |
| 3[a] | 2 | 1.1 | 1.3 | toluene, 50 | 20 |
| 4[c] | 25 | 14 | 16 | isooctane, 65 | 33 |

TABLE IV-continued

| Run | Alkenyl bromide, g | NaHCO$_3$, g | Pyridine-N—oxide, g | Solvent mL | Yield of cis-11-hexadecenal, mol % |
|---|---|---|---|---|---|
| 5$^c$ | 100 | 55 | 63 | diglyme, 100 | 60 |
| 6$^d$ | 50 | 27 | 32 | diglyme, 45 | 40 |
| 7$^c$ | 97.5 | 54 | 63 | none | 35 |
| 8$^b$ | 50 | 28 | 31 | Xylenes, 75 | 35 |
| 9$^c$ | 100 | 55 | 63 | diglyme, 100 | 55 |

Legend:
$^a$ = 100 mL reaction vessel
$^b$ = 300 mL reaction vessel
$^c$ = 500 mL reaction vessel
$^d$ = 1000 mL reaction vessel The results of these experiments recorded in Table IV demonstrate that cis-11-hexadecenal was prepared from cis-11-hexadecenyl bromide in the presence of pyridine-N-oxide, sodium bicarbonate and, optionally, solvent such as diglyme.

EXAMPLE XVIII

The sequence of reaction steps employed in the present invention was varied, so that the product alkynyl bromide of step (a) was first subjected to oxidation conditions (step (c')) and then reduced (step (b')). Thus, a 250 mL 3-necked round bottom flask was charged with 50 g (0.17 mol) of hexadecynyl bromide, 23.4 g of pyridine N-oxide (0.25 mol) and 13.9 g of NaHCO$_3$ (0.17 mol). Diglyme (50 mL) was added and the mixture heated to 120°–130° C. for about 3 hours. The cooled reaction mixture was added to about 200 mL of water, then extracted twice with 200 mL aliquots of diethyl ether. Isopropanol was added, as needed, to aid emulsion breaking. The organic layer was dried over MgSO$_4$, filtered and solvent removed on the rotary evaporator. Product was then recovered by vacuum distillation. A 45 mol % yield of hexadecynyl aldehyde with a boiling point of about 138° C. @ 0.2 mm Hg was recovered.

An aliquot (17.5 g) of the alkynyl aldehyde just prepared was subjected to typical hydrogenation conditions as described in Example XVI. Thus, the alkynyl aldehyde was dissolved in 200 mL of hexane and 1 g of 5 wt. % Pd on CaCO$_3$ with lead acetate modifier added. The typical nitrogen and hydrogen flush procedure described above was employed. The autoclave was maintained below 5° C., and a hydrogen pressure of 50 psig was employed. Reaction was quenched after an hour by purging the vessel contents with nitrogen. Catalyst was removed by filtration through a bed of Celite filter aid, solvent removed on the rotary evaporator, then product vacuum distilled. Analysis by glc, liquid chromatography and $^{13}$C-NMR reveal the trans content of the product to be less than 2 wt. %.

The experiments demonstrate that reaction steps (b) and (c) can be interchanged, if desired.

We claim:
1. A process for the preparation of an olefinic aldehyde having the formula:

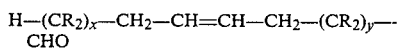

wherein x=0–20, inclusive, y=1–20, inclusive, and each R is independently h, C$_1$–C$_{20}$ alkyl, cycloalkyl, aryl, aralkyl, and alkaryl which comprises the steps of:
(a) reacting an α,ω-dihalide having the formula:

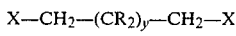

wherein X is Cl, Br or I, and Y and R are as defined above, with a metal acetylide having the formula:

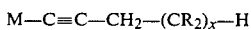

wherein M is Li or Na and x and R are as defined above to give a reaction product containing an acetylenic halide having the formula:

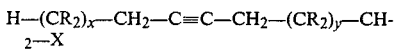

wherein x, y, R and X are defined above;
(b) oxidizing the acetylenic halide obtained in (a) to give an acetylenic aldehyde having the formula:

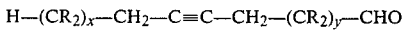

wherein x, y, R and X are as defined above; and
(c) hydrogenating the acetylenic aldehyde obtained in (b) with hydrogen and a selective hydrogenation catalyst to give said olefinic aldehyde.

2. A process according to claim 1 wherein the molar ratio of α,ω-dihalide to metal acetylide employed in step (a) is within the range of 1:1 to 4:1, wherein the α,ω-dihalide and metal acetylide are heated to a temperature in the range of about 90°–150° C. for a time in the range of about 2 to 8 hours in an inert atmosphere.

3. A process in accordance with claim 1 wherein the step (c) selective hydrogenation is carried out in the presence of hydrogen and a selective hydrogenation catalyst at a pressure in the range of about atmospheric to 200 psig, a temperature in the range of about −60° to 25° C. for a time in the range of about 0.5 to 8 hours.

4. A process according to claim 1 wherein step (a) is carried out in the presence of at least one promoter chosen from the group consisting of ethylene diamine, tetramethylene diamine, tetramethylurea, pyridine, dioxane, diglyme (diethylene glycol dimethyl ether), triglyme (triethylene glycol dimethyl ether), tetraglyme (tetraethylene glycol dimethyl ether), hexamethylphosphorus triamide, 1,3-dimethyl-3,4,5,6-tetrahydro-2(1H)-pyrimidinone and 1,3-dimethyl-2-imidazolidinone and mixtures thereof.

5. A process according to claim 4 wherein said promoter is chosen from the group consisting of diglyme (diethylene glycol dimethyl ether), triglyme (triethylene glycol dimethyl ether), tetraglyme (tetraethylene glycol dimethyl ether), hexamethylphosphorus triamide, 1,3-dimethyl-3,4,5,6-tetrahydro-2(1H)-pyrimidinone and 1,3-dimethyl-2-imidazolidinone and mixtures thereof.

6. A process according to claim 1 wherein said olefinic aldehyde is a cis-olefin of the formula:

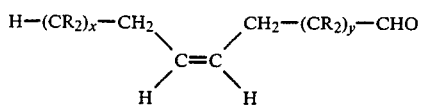

wherein x, y and R are as defined above.

7. A process according to claim 6 wherein $x=0-10$, $y=1-10$ and each R is independently H, $C_1$-$C_{10}$ alkyl, cycloalkyl, aryl, aralkyl and alkaryl.

8. A process according to claim 1 wherein said $\alpha,\omega$-dihalide in step (a) is employed in at least 1.2 molar excess compared to the amount of metal acetylide employed.

9. A process according to claim 1 wherein X is Br.

10. A process according to claim 1 wherein M is Li.

11. A process according to claim 1 wherein said selective hydrogenation catalyst is 5 wt. % Pd on $CaCO_3$ modified with $Pb(O_2CCH_3)_2$.

12. A process according to claim 1 wherein said oxidation is carried out by contacting the $—CH_2—X$ moiety of said acetylenic halide with an amine oxide and sodium bicarbonate.

* * * * *